United States Patent
Zaid et al.

(10) Patent No.: US 11,358,963 B2
(45) Date of Patent: Jun. 14, 2022

(54) LOW-TEMPERATURE SYNTHESIS OF THYMOQUINONE AND HARMALINE COMPOUNDS

(71) Applicant: Ankh Life Sciences Limited, Dublin (IE)

(72) Inventors: Gene H. Zaid, Hutchinson, KS (US); Beth Ann Wolf, Hutchinson, KS (US); Rachel Elizabeth Ropp, Hutchinson, KS (US)

(73) Assignee: Ankh Life Sciences Limited, Dublin (IE)

( * ) Notice: Subject to any disclaimer, the term of this patent is extended or adjusted under 35 U.S.C. 154(b) by 129 days.

(21) Appl. No.: 16/810,291

(22) Filed: Mar. 5, 2020

(65) Prior Publication Data

US 2021/0276998 A1 Sep. 9, 2021

(51) Int. Cl.
*C07D 471/04* (2006.01)

(52) U.S. Cl.
CPC .................. *C07D 471/04* (2013.01)

(58) Field of Classification Search
CPC .................................................. C07D 471/04
See application file for complete search history.

(56) References Cited

U.S. PATENT DOCUMENTS

| | | |
|---|---|---|
| 2,616,893 A | 11/1952 | Newby |
| 5,304,658 A | 4/1994 | Terao et al. |
| 9,630,899 B1 | 4/2017 | Huang et al. |
| 10,875,849 B2 | 12/2020 | Li et al. |
| 10,875,859 B2 * | 12/2020 | Zaid ................ A61P 35/00 |
| 2015/0037308 A1 | 2/2015 | Ikemoto et al. |
| 2019/0315742 A1 | 10/2019 | Zaid et al. |
| 2020/0101050 A1 | 4/2020 | Zaid et al. |
| 2020/0102305 A1 | 4/2020 | Zaid et al. |
| 2020/0102306 A1 | 4/2020 | Zaid et al. |

FOREIGN PATENT DOCUMENTS

WO 2019200107 A1 10/2019

OTHER PUBLICATIONS

International Search Report and Written Opinion in PCT/US2021/020847, filed Mar. 4, 2021.

\* cited by examiner

*Primary Examiner* — D Margaret M Seaman
(74) *Attorney, Agent, or Firm* — Hovey Williams LLP

(57) ABSTRACT

Low-temperature syntheses of thymoquinone/harmaline compounds are provided which give increased yields of desirable products having molecular weights of from about 360-380. The syntheses involve carrying out reactions between thymoquinone and harmaline and a non-interfering solvent at a temperature of less than about 10° C.

11 Claims, 11 Drawing Sheets

LOW-TEMPERATURE SYNTHESIS OF THYMOQUINONE AND HARMALINE COMPOUNDS

BACKGROUND OF THE INVENTION

Field of the Invention

The present invention is concerned with new synthesis methods for the preparation of thymoquinone/harmaline adducts or compounds. More particularly, the invention is concerned with low-temperature synthesis techniques which provide greater quantities of desirable thymoquinone/harmaline compounds having molecular weights of about 360 to 380.

SUMMARY OF THE INVENTION

US Patent Publication 2019/0315742 and U.S. patent application Ser. No. 16/701,554 filed Dec. 3, 2019 (both of which are incorporated by reference herein in their entireties), describe adducts or compounds of thymoquinone (TQ) and harmaline and related harmaline-like compounds. These reaction products show significant promise as treatments for human diabetes and cancers. These references teach that the adducts or compounds are prepared by mixing together TQ and harmaline (or harmaline-like material(s)) in an organic solvent, such as a C1-C4 lower alcohol (e.g., ethanol) and/or dimethyl sulfoxide (DMSO), followed by allowing the reaction mixture to stand for a period of from about 12 hours-4 weeks at a temperature ranging from about 20-60° C. The most preferred reaction conditions involve standing for 24 hours at room temperature. However, these reactions yield very low quantities of the desirable reaction products having molecular weights of 360, 376, and 378, normally less than 20% by weight. Furthermore, these higher temperature reactions lead to significant quantities of higher molecular weight species above MW 500, which must be separated from the desired end products.

The present invention overcomes these difficulties, and provides improved methods for synthesis of TQ/harmaline reaction products, in good yields. Generally speaking, the methods of the invention comprise the steps of mixing together thymoquinone and harmaline in a noninterfering solvent, and carrying out the reaction between thymoquinone and harmaline at a temperature of less than about 10° C. Desirably, the reaction temperature is less than about 0° C., and more preferably ranges from about −10° C. to about −100° C. The reaction time is usually for a period of from about 4 hours to about 14 days, and more preferably from about 6-100 hours. Advantageously, the low-temperature conditions are maintained throughout the reaction period.

The methods hereof preferably involve carrying out the TQ/harmaline reaction so that the amount of reaction products having a molecular weight ranging from about 360-380 is greater than the amount of any other reaction product of different molecular weight. Furthermore, at least about 35% by weight of the reaction products have molecular weights ranging from about 360-380. Still more preferably, the reactions are carried out so that the total amount of the reaction products having molecular weights of about 376 and about 378 is at least about 25% by weight of the reaction products, and more preferably at least about 30% by weight thereof. A variety of noninterfering solvents may be used in the invention, although those selected from the group consisting of a C1-C4 alcohol, dimethyl sulfoxide, and mixtures thereof, are preferred.

The desirable molecular weight reaction products may include tautomers and isomers, as explained below. Furthermore, the reaction products may be readily modified or derivatized to provide solvates, esters, metal complexes (e.g., Cu, Fe, Zn, Pt, V), and salts of the reaction products.

DETAILED DESCRIPTION OF THE PREFERRED EMBODIMENTS

Figure 1:
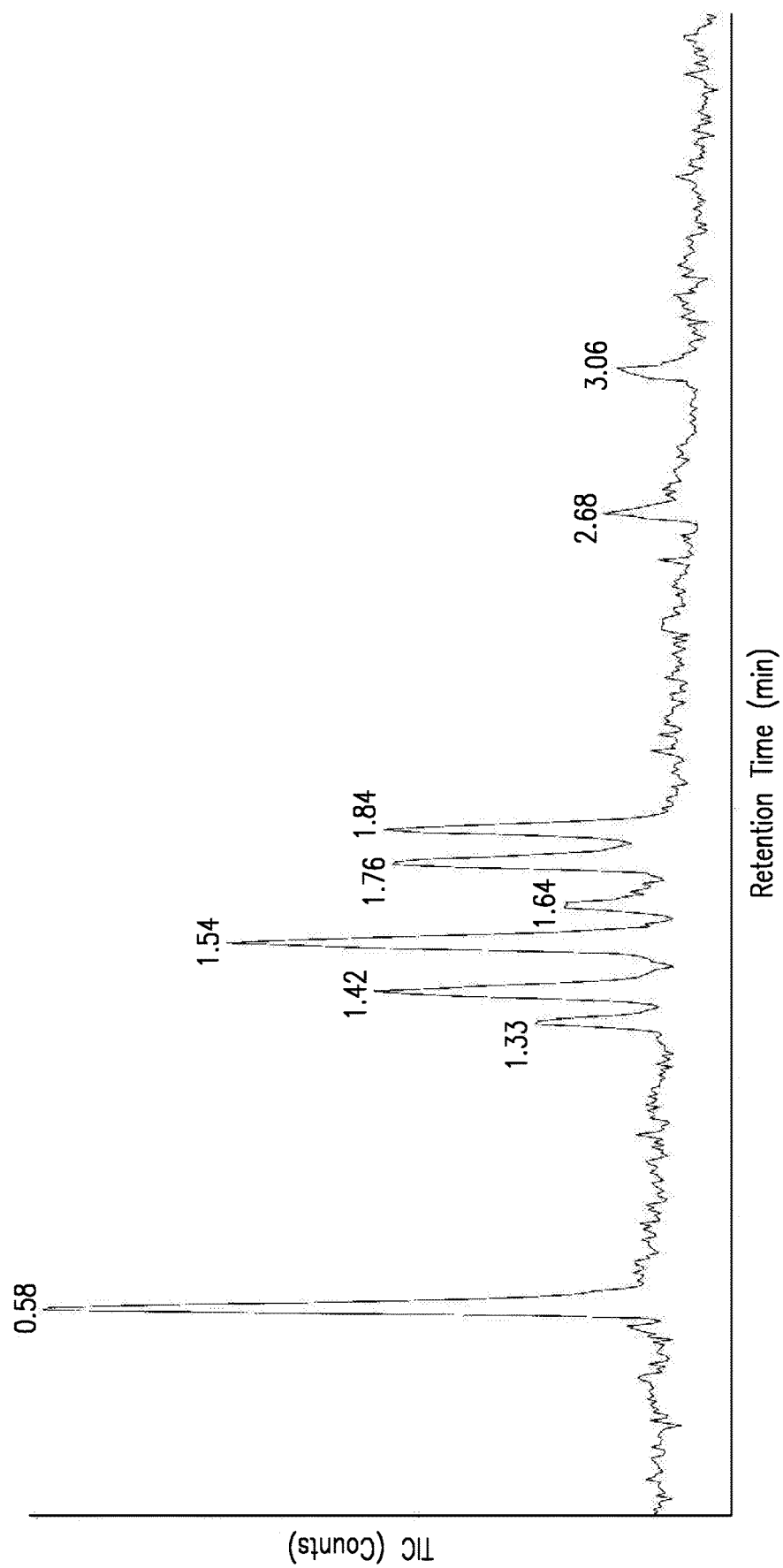
FIG. 1 is a spectrum derived from the assay described in Example 1.

Thymoquinone, C10H12O2, is identified as CAS #490-91-5, and has a molecular weight of 164.2. It has the structure

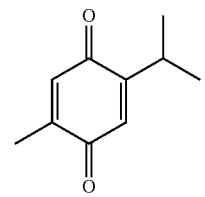

Harmaline (7-methoxy-1-1-methyl-4,9-dihydro-3H-pyrido[3,4-b]indole) is a fluorescent psychoactive alkaloid from the group of harmala alkaloids and β-carbolines, and occurs in various plants, such as *Peganum harmala*. Harmaline is identified as CAS #304-21-2, and exists in two tautomeric forms:

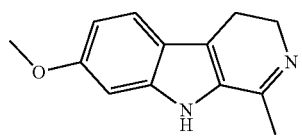

7-methoxy-1-methyl-4,9-dihydro-3H-pyrido[3,4-b]indole
Chemical Formula: $C_{13}H_{14}N_2O$
Exact Mass: 214.11

-continued

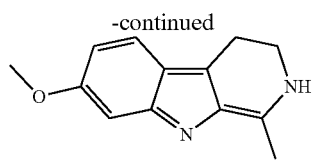

7-methoxy-1-methyl-3,4-dihydro-2H-pyrido[3,4-b]indole
Chemical Formula: $C_{13}H_{14}N_2O$
Exact Mass: 214.11

As used herein, "harmaline" refers to either or both tautomers.

In preparing the reaction product compositions of the invention, use should be made of ingredients of relatively high purity, typically at least about 90% by weight pure, and more preferably at least about 98% by weight pure. The use of naturally occurring sources for the ingredients is generally not appropriate or desirable, because these naturally occurring products contain relatively small amounts of the desired components and/or have potentially interfering compounds therein. Use of low-purity ingredients often leads to little or no reaction products in accordance with the invention.

Thus, the preferred TQ and harmaline starting compounds or components of the invention are either synthetically derived or derived from one or more naturally occurring product(s) which have been significantly modified so as to contain at least about 90% by weight (more preferably at least about 98% by weight) of the desired component. As used herein, "synthetically derived" means that the component in question was synthesized using specific starting ingredients and one or more chemical and/or biological reactions to obtain substantially pure compounds. Modification of naturally occurring products may involve extractions, or any other physical or chemical steps to achieve the desired end product.

TQ/Harmaline Reaction Products

An analysis of the reaction products reveals that some products described below have molecular weights of about 378, and which may exist in equilibrium with dehydrated versions having molecular weights of about 360 (all molecular weights reported herein were derived using conventional liquid chromatography/mass spectrometry techniques). Structures I-VII below illustrate various forms of these reaction products, where Structures I-IV are isomers, and Structure VII is a dehydrated version of Structure VI.

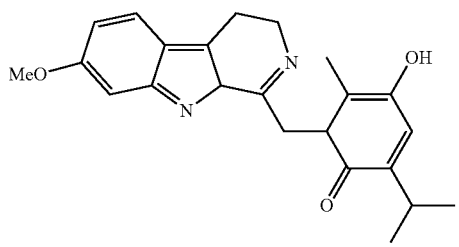

I 4-hydroxy-2-isopropyl-6-((7-methoxy-4,9a-dihydro-3H-pyrido
[3,4-b]indol-1-yl)methyl)-5-
methylcyclohexa-2,4-dien-1-one
Chemical Formula: $C_{23}H_{26}N_2O_3$
Exact Mass: 378.19

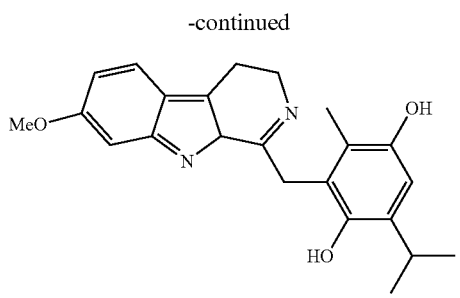

II 5-isopropyl-3-((7-methoxy-4,9a-dihydro-3H-pyrido[3,4-b]indol-1-
yl)methyl)-2-methylbenzene-1,4-diol
Chemical Formula: $C_{23}H_{26}N_2O_3$
Exact Mass: 378.19

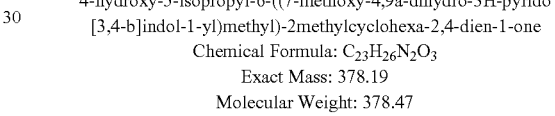

III 4-hydroxy-5-isopropyl-6-((7-methoxy-4,9a-dihydro-3H-pyrido
[3,4-b]indol-1-yl)methyl)-2methylcyclohexa-2,4-dien-1-one
Chemical Formula: $C_{23}H_{26}N_2O_3$
Exact Mass: 378.19
Molecular Weight: 378.47

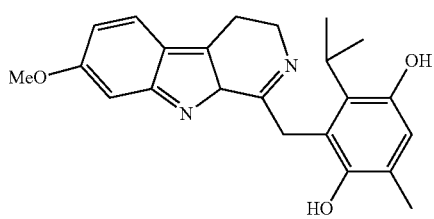

IV 2-isopropyl-3-((7-methoxy-4,9a-dihydro-3H-pyrido[3,4-b]indol-1-
yl)methyl)-5-methylbenzene-1,4-diol
Chemical Formula: $C_{23}H_{26}N_2O_3$
Exact Mass: 378.19

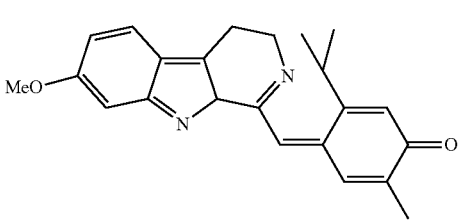

V (Z)-5-isopropyl-4-((7-methoxy-4,9a-dihydro-3H-pyrido
[3,4-b]indol-1-yl)methylene)-2-methylcyclohexa-2,5-dien-1-one
Chemical Formula: $C_{23}H_{24}N_2O_2$
Exact Mass: 360.18

-continued

VI

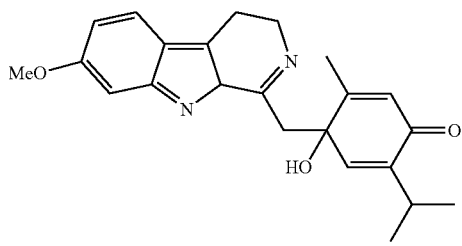

4-hydroxy-2-isopropyl-4-((7-methoxy-4,9a-dihydro-3H-pyrido
[3,4-b]indol-1-yl)methyl)-5-methylcyclohexa-2,5-dien-1-one
Chemical Formula: $C_{23}H_{26}N_2O_3$
Exact Mass: 378.19

VII

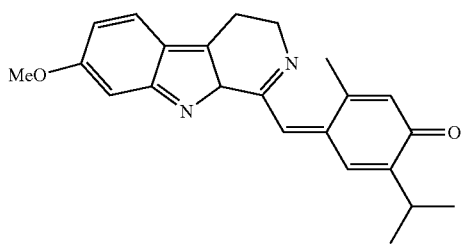

(Z)-2-isopropyl-4-((7-methoxy-4,9a-dihydro-3H-pyrido
[3,4-b]indol-1-yl)methylene)-5-methylcyclohexa-2,5-dien-1-one
Chemical Formula: $C_{23}H_{24}N_2O_2$
Exact Mass: 360.18

Other possible structures include:

IA

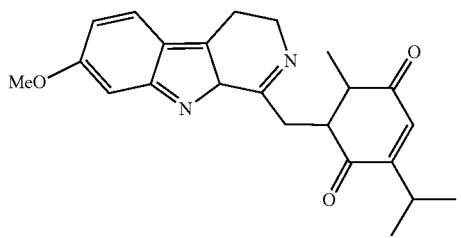

2-isopropyl-6-((7-methoxy-4,9a-dihydro-3H-pyrido[3,4-b]indol-1-yl)
methyl)-5-methylcyclohex-2-ene-1,4-dione
Chemical Formula $C_{23}H_{26}N_2O_3$
Exact Mass: 378.19

IIIA

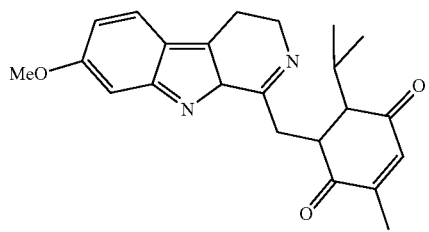

5-isopropyl-6-((7-methoxy-4,9a-dihydro-3H-pyrido[3,4-b]indol-1-yl)
methyl)-2-methylcyclohex-2-ene-1,4-dione
Chemical Formula $C_{23}H_{26}N_2O_3$
Exact Mass: 378.19
Molecular Weight: 378.47

The above reaction products are characterized by a single thymoquinone moiety and a single harmaline or harmaline-like moiety. These predominate during the initial stages of the reactions. In these reactions, the substituent of the pyridyl ring of harmaline reacts at an unsubstituted carbon atom which is alpha to either of the carbonyl groups of TQ. This phenomenon is illustrated in Structures I-IV above. In another reaction scheme, the substituent of the pyridyl ring of harmaline reacts directly with either of the carbonyl groups of TQ. These types of reactions are illustrated in Structures V-VII above.

The thermodynamic properties of the harmaline and TQ reactants and reaction products I-IV isomers (MW 378) were used to obtain reaction energetics using Density Functional Theory (DFT). Additional calculations were used to determine enthalpy, entropy, and Gibbs free energy values for the reactions. Reaction products II and IV were found to be the most thermodynamically favorable and smaller free energy values. Reaction product II was deemed to be the most stable and had the lowest free energy value. Note that compounds II and IV are characterized by reaction of the pyridyl ring methyl substituent with one of the two unsubstituted carbon atoms alpha to a corresponding carbonyl carbon, and two hydroxyl substituents on the TQ ring.

However, if the reaction mixtures are allowed to set for an extended period of time, e.g., from about 3-30 days, other reaction products having higher molecular weights of about 542, or in oxidized forms, about 540 are formed as the predominant reaction product. These reaction products are characterized by the presence of two thymoquinone moieties and a single harmaline or harmaline-like moiety. These same types of higher molecular weight species can be obtained if, after the initial reaction to yield the 378/360 MW products I-VII, the reaction mixtures are refluxed for a period of from about 30-120 minutes.

In particular, the MW 542 reaction products, and their oxidized MW 540 reaction products, formed by the reaction between thymoquinone and harmaline are set forth below as compounds VIIIA-VIIIF:

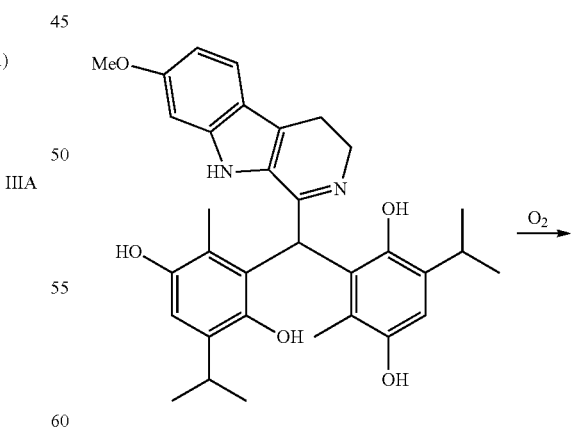

VIIIA
3,3'-((7-methoxy-4,9-dihydro-3H-pyrido[3,4-b]indol-1-yl)methylene)bis(5-isopropyl-2-methylbenzene-1,4-diol)
Chemical Formula: $C_{33}H_{38}N_2O_5$
Exact Mass: 542.28
Molecular Weight: 542.68

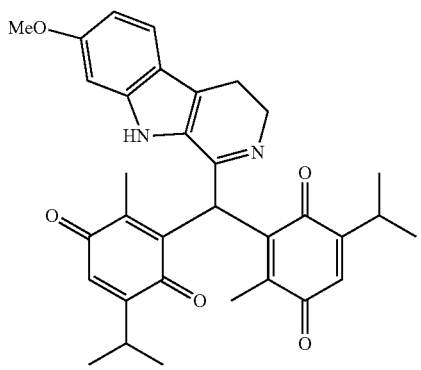

VIIIB
3,3'-((7-methoxy-4,9-dihydro-3H-pyrido[3,4-b]indol-1-yl)
methylene)bis(5-isopropyl-2-methylcyclohexa-2,5-diene-1,4-dione)
Chemical Formula: $C_{33}H_{34}N_2O_5$
Exact Mass: 538.25
Molecular Weight: 538.64

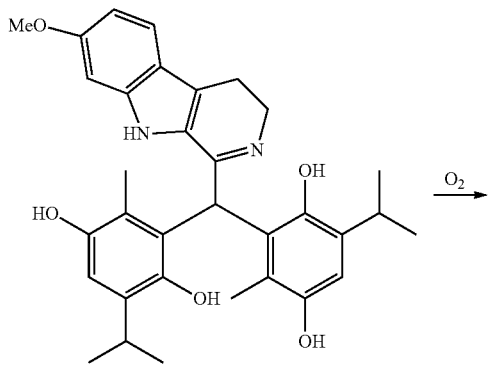

VIIIC
3,3'-((7-methoxy-4,9-dihydro-3H-pyrido[3,4-b]indol-1-
yl)methylene)bis(5-isopropyl-2-methylbenzene-1,4-diol)
Chemical Formula: $C_{33}H_{38}N_2O_5$
Exact Mass: 542.28
Molecular Weight: 542.68

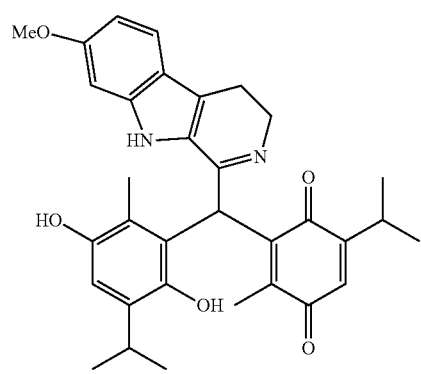

VIIID
3-((2,5-dihydroxy-3-isopropyl-6-methylphenyl)(7-methoxy-4,9-
dihydro-3H-pyrido[3,4-b]indol-1-yl)methyl)-5-isopropyl-2-
methylcyclohexa-2,5-diene-1,4-dione
Chemical Formula: $C_{33}H_{36}N_2O_5$
Exact Mass: 540.26
Molecular Weight: 540.66

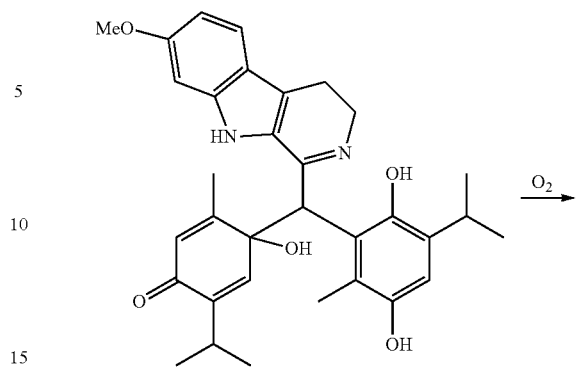

VIIIE
4-((2,5-dihydroxy-3-isopropyl-6-methylphenyl)(7-methoxy-4,9-
dihydro-3H-pyrido[3,4-b]indol-1-yl)methyl)-4-hydroxy-2-isopropyl-
5-methylcyclohexa-2,5-dien-1-one
Chemical Formula: $C_{33}H_{38}N_2O_5$
Exact Mass: 542.28
Molecular Weight: 542.68

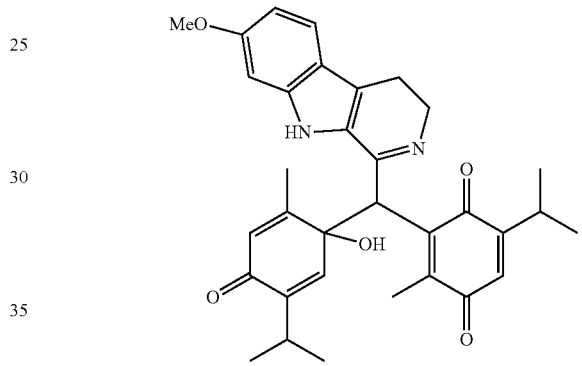

VIIIF
3-((1-hydroxy-5-isopropyl-2-methyl-4-oxocyclohexa-2,5-dien-1-
yl)(7-methoxy-4,9-dihydro-3H-pyrido[3,4-b]indol-1-yl)methyl)-
5-isopropyl-2-methylcyclohexa-2,5-diene-1,4-dione
Chemical Formula: $C_{33}H_{36}N_2O_5$
Exact Mass: 540.26
Molecular Weight: 540.66

Presently, compounds II and IV above are deemed to be the most active, particularly in the context of diabetes.

EXAMPLES

A series of low temperature thymoquinone/harmaline syntheses were undertaken to determine the principal products synthesized by molecular weight, and the quantity thereof as compared with byproducts. Generally speaking, each test involved dissolving respective quantities of thymoquinone and harmaline in absolute ethanol, allowing the reaction to occur at different low temperature levels, and then analyzing the reaction products with a G2XS Liquid Chromatography-Mass Spectrometry (LCMS). Specifically, use was made of a Waters G2XS LCMS system with ACQUITY UPLC BEH C18 Column, 130 Å, 1.7 μm, 2.1 mm×100 mm, under the below-listed conditions. The "mass" referred to in the examples is the molecular weight of the products as derived from the LCMS. A spectrum from each test is set forth in the drawings.

Example 1: 1:2-80° C.

A. Ingredients
   164 mg thymoquinone
   107 mg harmaline
   2 mL EtOH
B. Reaction Conditions
   1. Combine thymoquinone, harmaline, and ethanol
   2. Mix until dissolved
   3. Put in −80° C. freezer over the weekend
   4. Remove from freezer and allow sample to return to room temperature
   5. Add 5 μL of sample to 1 mL of EtOH, with mixing
   6. Add 10 μL of dilution to 0.75 mL LCMS grade water and 0.25 mL of LCMS grade acetonitrile

| LCMS column gradient: | | | |
| --- | --- | --- | --- |
| Solvent A | Water with 1% Formic Acid | | |
| Solvent B | Acetonitrile with 1% Formic Acid | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

FIG. 1 is the spectrum generated in this example. The following table lists the retention times, the areas under the important peaks, the % areas, and the mass of the corresponding reaction products.

| Retention Time (min) | Area | % Area | Mass |
| --- | --- | --- | --- |
| 0.58 | 36621729 | 25.50 | 214 |
| 1.33 | 6893008 | 4.80 | 378 |
| 1.42 | 19932648 | 13.88 | 378 |
| 1.54 | 29866114 | 20.80 | 378 |
| 1.64 | 5479588 | 3.82 | 378 |
| 1.76 | 18950909 | 13.20 | 360 |
| 1.84 | 16542199 | 11.52 | 376 |
| 2.68 | 4322666 | 3.01 | 524 |
| 3.06 | 4979449 | 3.47 | 522 |

With approximately 54.82% with the mass 378/376.

Example 2: 1:2-80° C.

A. Ingredients
   164 mg thymoquinone
   107 mg harmaline
   2 mL EtOH
B. Reaction Conditions
   1. Combine thymoquinone, harmaline, and ethanol
   2. Mix until dissolved
   3. Put in −80° C. freezer over the weekend
   4. Remove from freezer and allow sample to return to room temperature
   5. Add 2 mL of water
   6. Filter using Whatman 1 filter paper
   7. Wash with water
   8. Dry in oven at 90° C.
   9. Add 2 μg of sample to 1 mL of EtOH, with mixing
   10. Add 10 μL of dilution to 0.75 mL LCMS grade water and 0.25 mL of LCMS grade acetonitrile

| LCMS column gradient: | | | |
| --- | --- | --- | --- |
| Solvent A | Water with 1% Formic Acid | | |
| Solvent B | Acetonitrile with 1% Formic Acid | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 2:
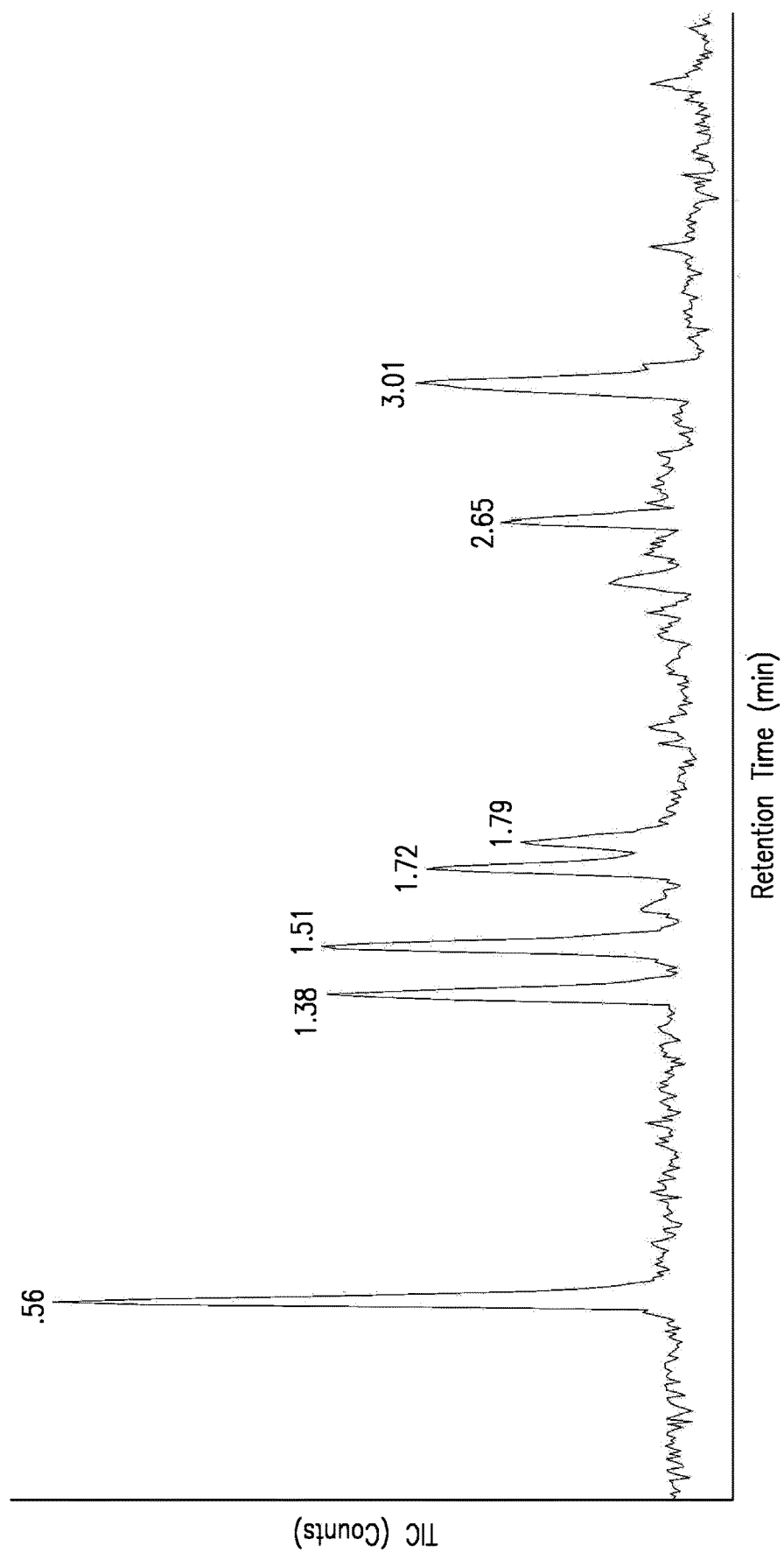
FIG. 2 is a spectrum derived from the assay described in Example 2.

FIG. 2 is the spectrum generated in this example. The following table lists the retention times, the areas under the important peaks, the % areas, and the mass of the corresponding reaction products.

| Retention Time (min) | Area | % Area | Mass |
| --- | --- | --- | --- |
| 0.56 | 30846712 | 25.93 | 214 |
| 1.38 | 18207142 | 15.30 | 378 |
| 1.51 | 20666195 | 17.37 | 378 |
| 1.72 | 12902678 | 10.84 | 360 |
| 1.79 | 8481740 | 7.13 | 358 |
| 2.65 | 7825410 | 6.58 | 524 |
| 3.01 | 20048072 | 16.85 | 522 |

With approximately 32.67% with the mass 378/3776.

Example 3: 1:3-18° C.

A. Ingredients
   164 mg thymoquinone
   71 mg harmaline
   2 mL EtOH
B. Reaction Conditions
   1. Combine thymoquinone, harmaline, and ethanol
   2. Mix until dissolved
   3. Put in −18° C. freezer overnight
   4. Remove from freezer and allow sample to return to room temperature
   5. Add 5 μL of sample to 1 mL of EtOH, with mixing
   6. Add 10 μL of dilution to 0.75 mL LCMS grade water and 0.25 mL of LCMS grade acetonitrile

| LCMS column gradient: | | | |
| --- | --- | --- | --- |
| Solvent A | Water with 1% Formic Acid | | |
| Solvent B | Acetonitrile with 1% Formic Acid | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 3:
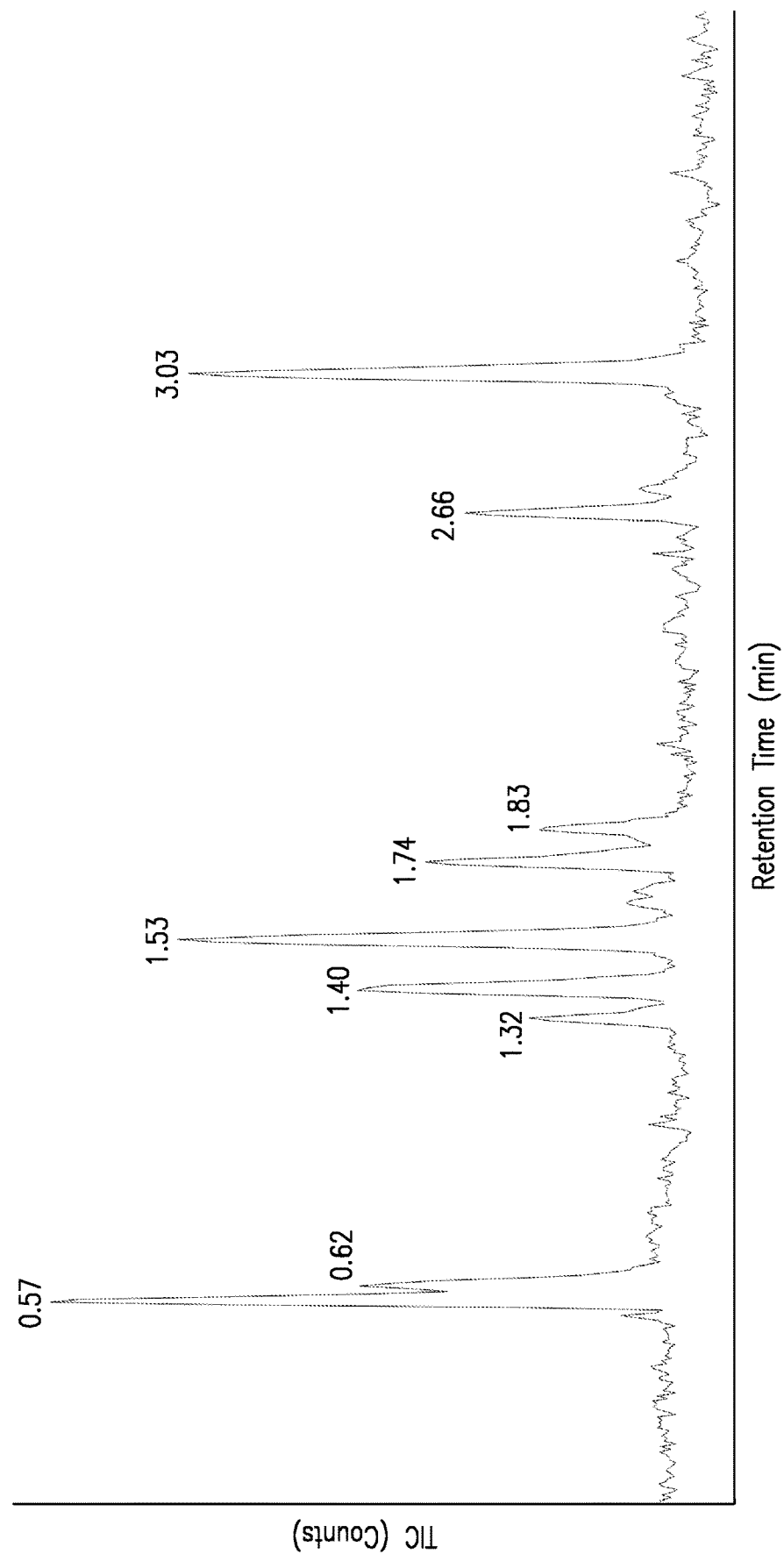
FIG. 3 is a spectrum derived from the assay described in Example 3.

FIG. 3 is the spectrum generated in this example. The following table lists the retention times, the areas under the important peaks, the % areas, and the mass of the corresponding reaction products.

| Retention Time (min) | Area | % Area | Mass |
| --- | --- | --- | --- |
| 0.57 | 29778554 | 17.69 | 214 |
| 0.61 | 17028809 | 10.12 | 212 |
| 1.32 | 6585566 | 3.91 | 378 |
| 1.4 | 20057868 | 11.92 | 378 |

-continued

| Retention Time (min) | Area | % Area | Mass |
|---|---|---|---|
| 1.53 | 31448269 | 18.68 | 378 |
| 1.74 | 14261852 | 8.47 | 360 |
| 1.83 | 8627882 | 5.13 | 376 |
| 2.66 | 10994085 | 6.53 | 524 |
| 3.03 | 29542138 | 17.55 | 522 |

With approximately 39.64% with the mass 378/376.

Example 4: 1:3-40° C.

A. Ingredients
  164 mg thymoquinone
  71 mg harmaline
  2 mL EtOH
B. Reaction Conditions
  1. Combine thymoquinone, harmaline, and ethanol
  2. Mix until dissolved
  3. Put in −40° C. freezer overnight
  4. Remove from freezer and allow sample to return to room temperature
  5. Add 5 μL of sample to 1 mL of EtOH, with mixing
  6. Add 10 μL of dilution to 0.75 mL LCMS grade water and 0.25 mL of LCMS grade acetonitrile

| LCMS column gradient: | | | |
|---|---|---|---|
| Solvent A | Water with 1% Formic Acid | | |
| Solvent B | Acetonitrile with 1% Formic Acid | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 4:
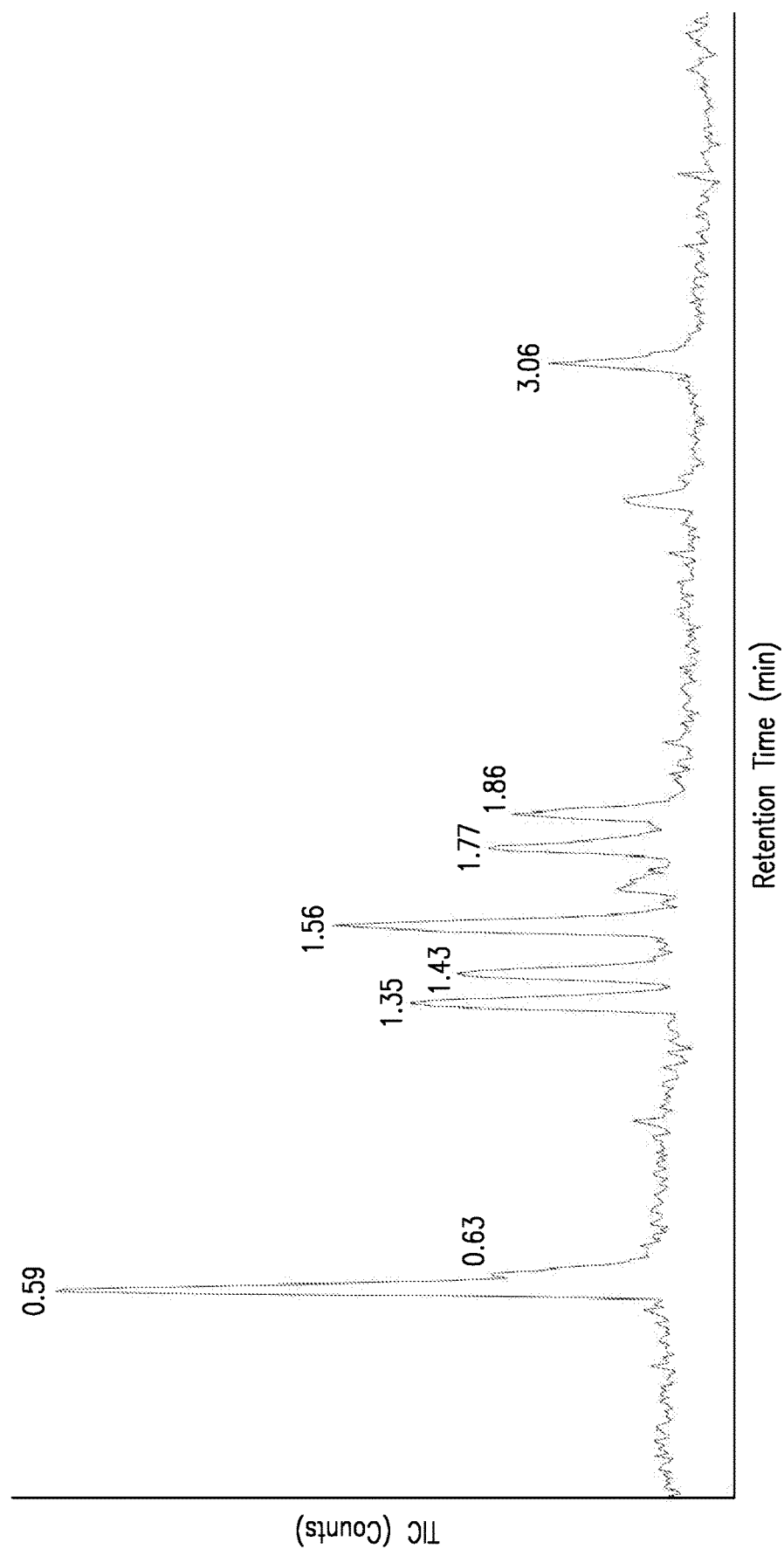
FIG. 4 is a spectrum derived from the assay described in Example 4.

FIG. 4 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.59 | 40034081 | 28.57 | 214 |
| 0.63 | 9609766 | 6.86 | 212 |
| 1.35 | 18016352 | 12.86 | 378 |
| 1.43 | 13867846 | 9.90 | 378 |
| 1.56 | 24944402 | 17.80 | 378 |
| 1.77 | 13657818 | 9.75 | 360 |
| 1.86 | 11976333 | 8.55 | 376 |
| 3.06 | 8026291 | 5.73 | 522 |

With approximately 49.10% with the mass 378/376.

Example 5: 1:3-80° C.

A. Ingredients
  164 mg thymoquinone
  71 mg harmaline
  2 mL EtOH
B. Reaction Conditions
  1. Combine thymoquinone, harmaline, and ethanol
  2. Mix until dissolved
  3. Put in −80° C. freezer over the weekend
  4. Remove from freezer and allow sample to return to room temperature
  5. Add 5 μL of sample to 1 mL of EtOH, with mixing
  6. Add 10 μL of dilution to 0.75 mL LCMS grade water and 0.25 mL of LCMS grade acetonitrile

| LCMS column gradient: | | | |
|---|---|---|---|
| Solvent A | Water with 1% Formic Acid | | |
| Solvent B | Acetonitrile with 1% Formic Acid | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 5:
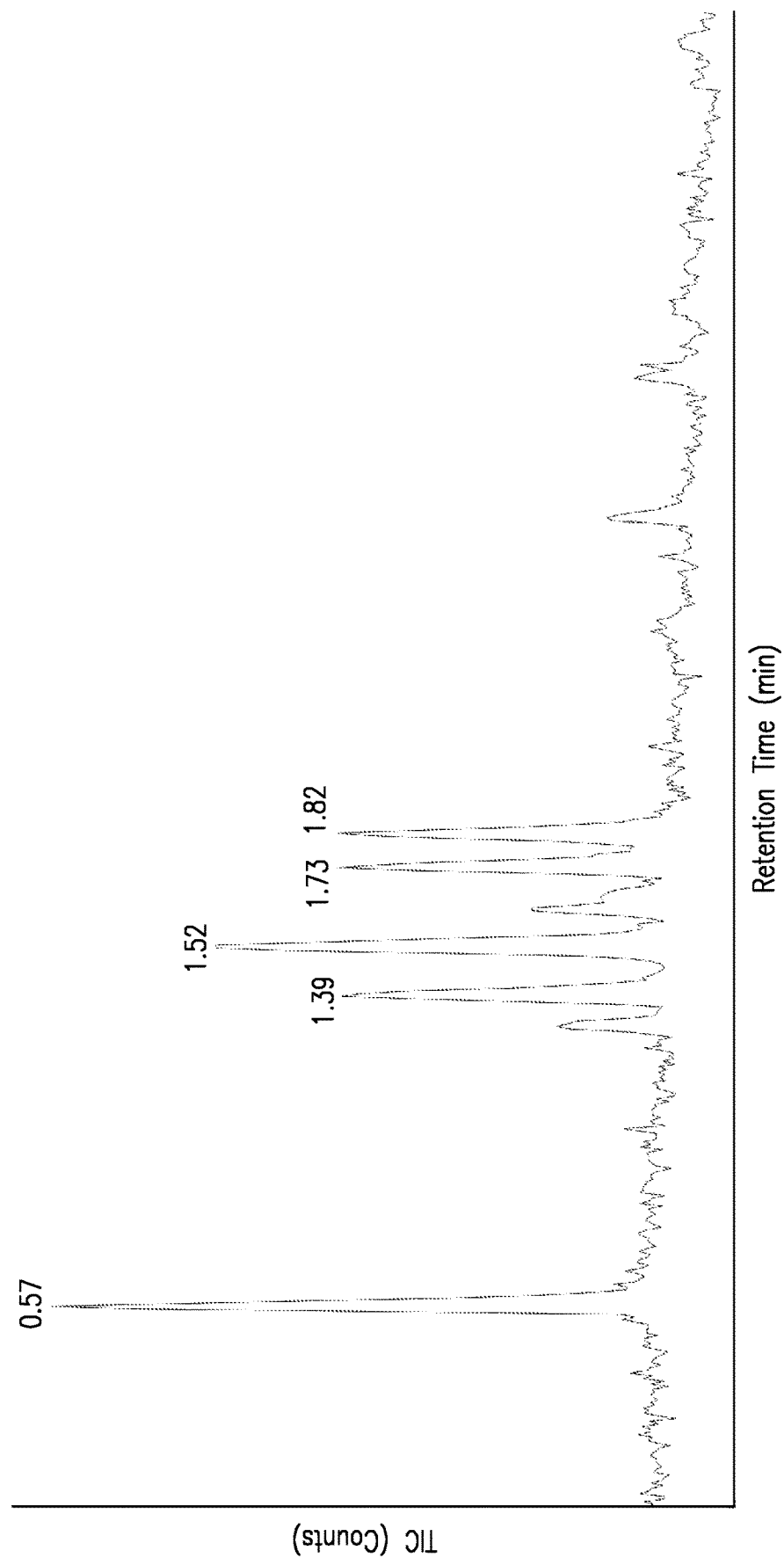
FIG. 5 is a spectrum derived from the assay described in Example 5.

FIG. 5 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.57 | 25905457 | 25.81 | 214 |
| 1.39 | 17198024 | 17.14 | 378 |
| 1.52 | 24367377 | 24.28 | 378 |
| 1.73 | 16657357 | 16.60 | 360 |
| 1.82 | 16232218 | 16.17 | 376 |

With approximately 57.59% with the mass 378/376.

Example 6: 1:3-80° C.

A. Ingredients
  164 mg thymoquinone
  71 mg harmaline
  2 mL EtOH
B. Reaction Conditions
  1. Combine thymoquinone, harmaline, and ethanol
  2. Mix until dissolved
  3. Put in −80° C. freezer over the weekend
  4. Remove from freezer and allow sample to return to room temperature
  5. Add 2 mL of water
  6. Filter using Whatman 1 filter paper
  7. Wash with water
  8. Dry in oven at 90° C.
  9. Add 2 μg of sample to 1 mL of EtOH, with mixing
  10. Add 10 μL of dilution to 0.75 mL LCMS grade water and 0.25 mL of LCMS grade acetonitrile

| LCMS column gradient: | | | |
|---|---|---|---|
| Solvent A | Water with 1% Formic Acid | | |
| Solvent B | Acetonitrile with 1% Formic Acid | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 6:
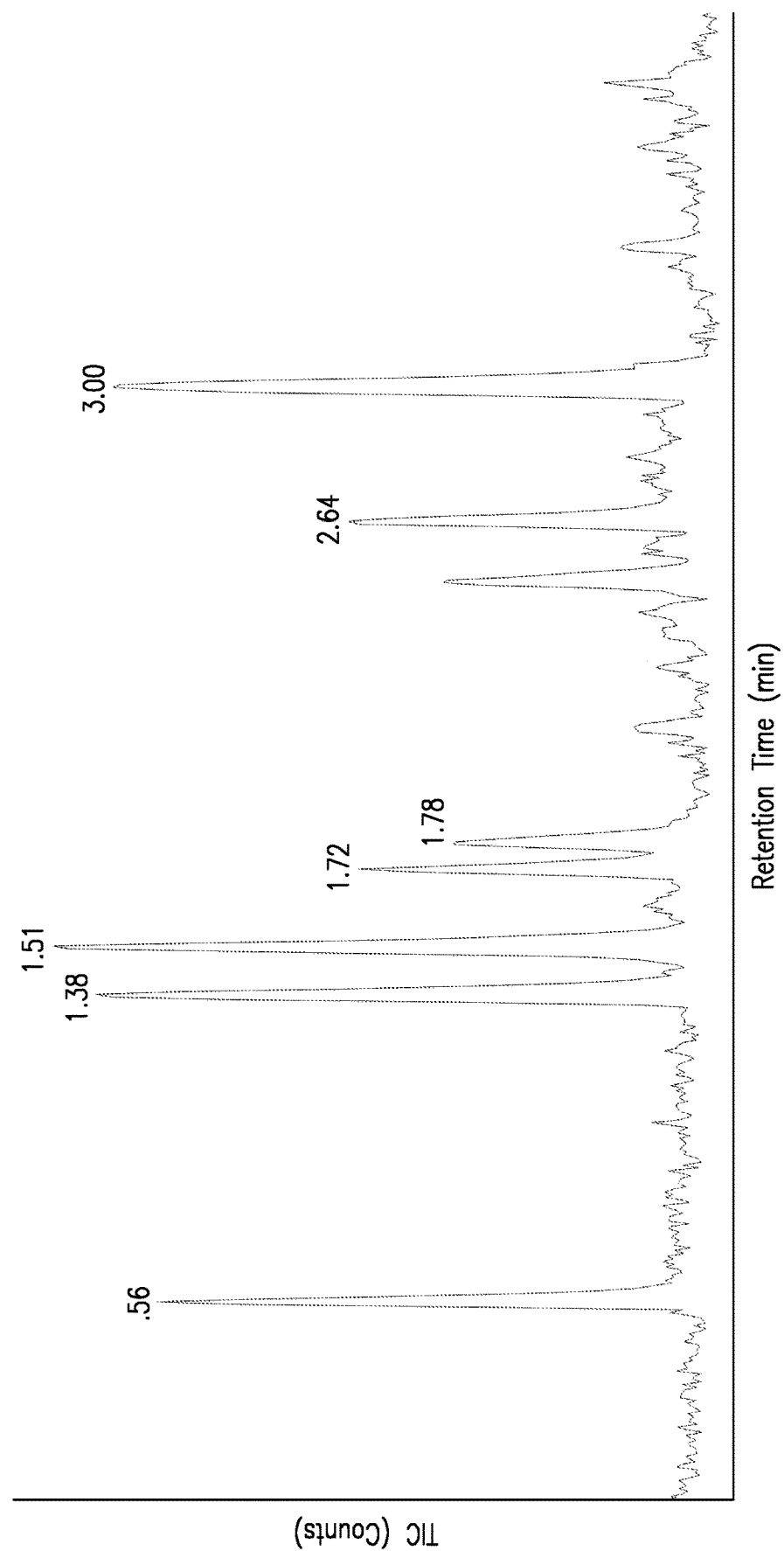
FIG. 6 is a spectrum derived from the assay described in Example 6.

FIG. 6 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.56 | 20011667 | 13.93 | 214 |
| 1.38 | 25631888 | 17.84 | 378 |
| 1.51 | 27886772 | 19.41 | 378 |
| 1.72 | 12421688 | 8.65 | 360 |
| 1.78 | 10883184 | 7.58 | 358 |
| 2.64 | 13547985 | 9.43 | 524 |
| 3.00 | 33279299 | 23.16 | 520 |

With approximately 37.25% with the mass 378.

Example 7: 1:4-18° C.

A. Ingredients
   164 mg thymoquinone
   71 mg harmaline
   2 mL EtOH
B. Reaction Conditions
   1. Combine thymoquinone, harmaline, and ethanol
   2. Mix until dissolved
   3. Put in −18° C. freezer overnight
   4. Remove from freezer and allow sample to return to room temperature
   5. Add 5 µL of sample to 1 mL of EtOH, with mixing
   6. Add 10 µL of dilution to 0.75 mL LCMS grade water and 0.25 mL of LCMS grade acetonitrile

| LCMS column gradient: | | | |
|---|---|---|---|
| Solvent A | Water with 1% Formic Acid | | |
| Solvent B | Acetonitrile with 1% Formic Acid | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 7:
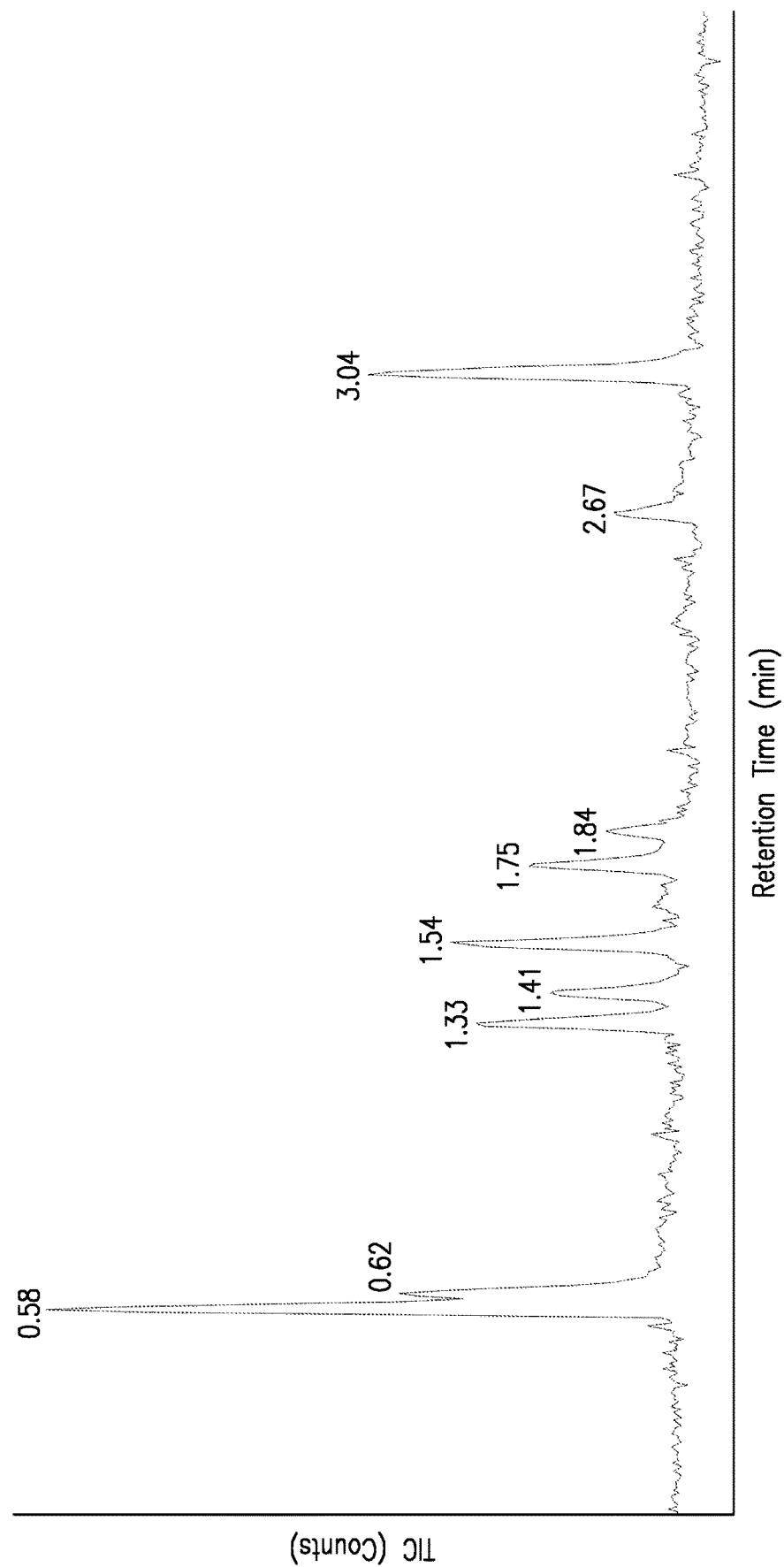
FIG. 7 is a spectrum derived from the assay described in Example 7.

FIG. 7 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.58 | 33397537 | 27.90 | 214 |
| 0.62 | 15245046 | 12.73 | 212 |
| 1.33 | 11140537 | 9.31 | 378 |
| 1.41 | 7669979 | 6.41 | 378 |
| 1.54 | 14070248 | 11.75 | 378 |
| 1.75 | 9269099 | 7.74 | 360 |
| 1.84 | 3980743 | 3.33 | 376 |
| 2.67 | 3893721 | 3.25 | 524 |
| 3.04 | 21045051 | 17.58 | 522 |

With approximately 30.79% with the mass 378/376.

Example 8: 1:4-40° C.

A. Ingredients
   164 mg thymoquinone
   71 mg harmaline
   2 mL EtOH
B. Reaction Conditions
   1. Combine thymoquinone, harmaline, and ethanol
   2. Mix until dissolved
   3. Put in −40° C. freezer overnight
   4. Remove from freezer and allow sample to return to room temperature
   5. Add 5 µL of sample to 1 mL of EtOH, with mixing
   6. Add 10 µL of dilution to 0.75 mL LCMS grade water and 0.25 mL of LCMS grade acetonitrile

| LCMS column gradient: | | | |
|---|---|---|---|
| Solvent A | Water with 1% Formic Acid | | |
| Solvent B | Acetonitrile with 1% Formic Acid | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 8:
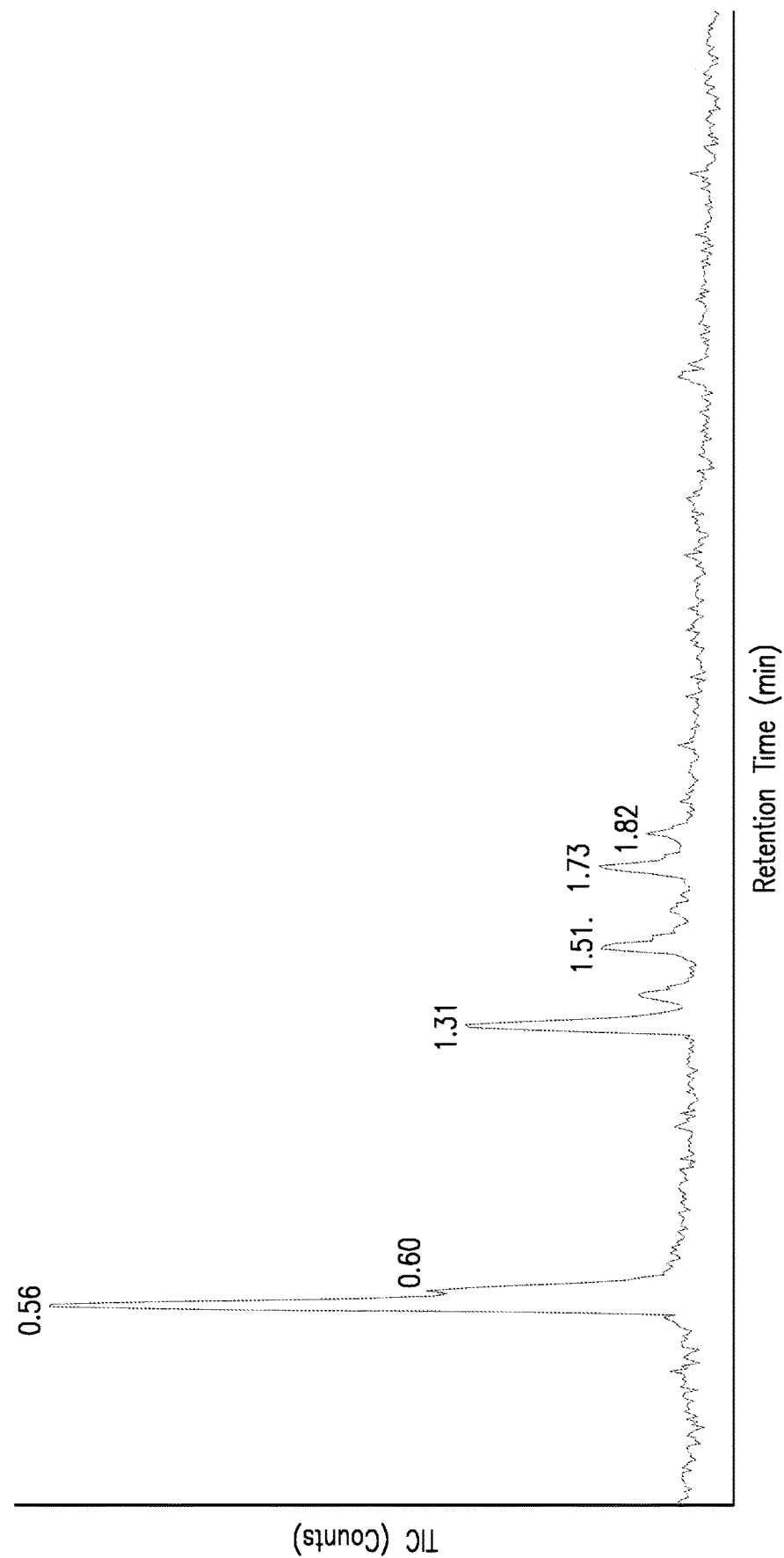
FIG. 8 is a spectrum derived from the assay described in Example 8.

FIG. 8 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.56 | 45002318 | 50.26 | 214 |
| 0.6 | 12944409 | 14.46 | 212 |
| 1.31 | 15085031 | 16.85 | 378 |
| 1.51 | 7349874 | 8.21 | 378 |
| 1.73 | 6674622 | 7.45 | 360 |
| 1.82 | 2480652 | 2.77 | 376 |

With approximately 27.83% with the mass 378/376.

Example 9: 1:4-80° C.

A. Ingredients
   164 mg thymoquinone
   54 mg harmaline
   2 mL EtOH
B. Reaction Conditions
   1. Combine thymoquinone, harmaline, and ethanol.
   2. Mix until dissolved
   3. Put in −80° C. freezer over the weekend
   4. Remove from freezer and allow sample to return to room temperature
   5. Add 5 µL of sample to 1 mL of EtOH, with mixing
   6. Add 10 µL of dilution to 0.75 mL LCMS grade water and 0.25 mL of LCMS grade acetonitrile

| LCMS column gradient: | | | |
|---|---|---|---|
| Solvent A | Water with 1% Formic Acid | | |
| Solvent B | Acetonitrile with 1% Formic Acid | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 9:
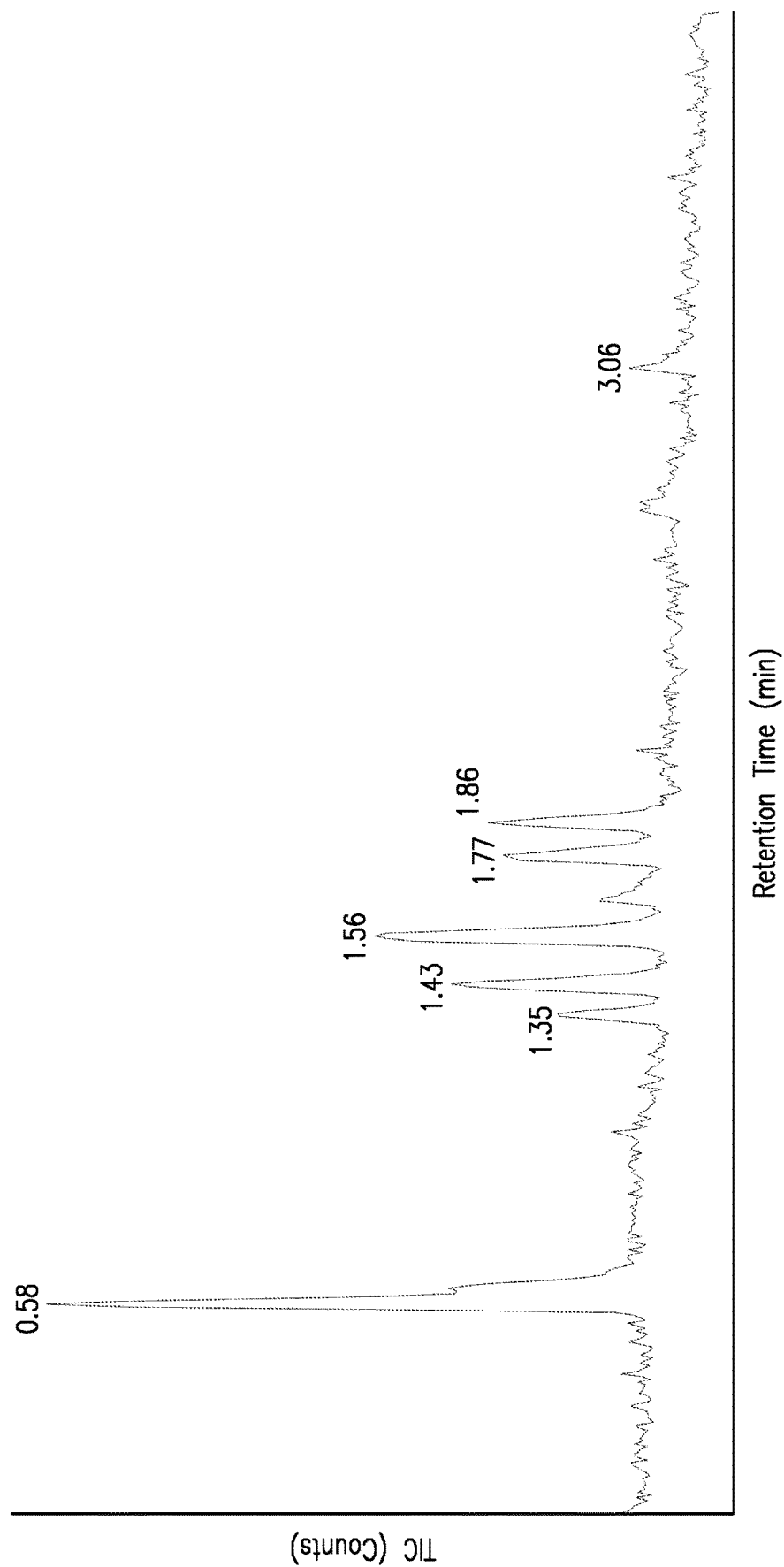
FIG. 9 is a spectrum derived from the assay described in Example 9.

FIG. 9 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.58 | 48542947 | 39.91 | 214 |
| 1.35 | 7395644 | 6.08 | 378 |
| 1.43 | 15222145 | 12.51 | 378 |
| 1.56 | 22264205 | 18.30 | 378 |
| 1.77 | 11909187 | 9.79 | 360 |
| 1.86 | 11332628 | 9.32 | 376 |
| 3.06 | 4979449 | 4.09 | 524 |

With approximately 46.21% with the mass 378/376.

Example 10: 1:5-80° C.

A. Ingredients
  164 mg thymoquinone
  43 mg harmaline
  2 mL EtOH
B. Reaction Conditions
  1. Combine thymoquinone, harmaline, and ethanol
  2. Mix until dissolved
  3. Put in −80° C. freezer overnight
  4. Remove from freezer and allow sample to return to room temperature
  5. Add 5 µL of sample to 1 mL of EtOH, with mixing
  6. Add 10 µL of dilution to 0.75 mL LCMS grade water and 0.25 mL of LCMS grade acetonitrile

| LCMS column gradient: | | | |
|---|---|---|---|
| Solvent A | Water with 1% Formic Acid | | |
| Solvent B | Acetonitrile with 1% Formic Acid | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 10:
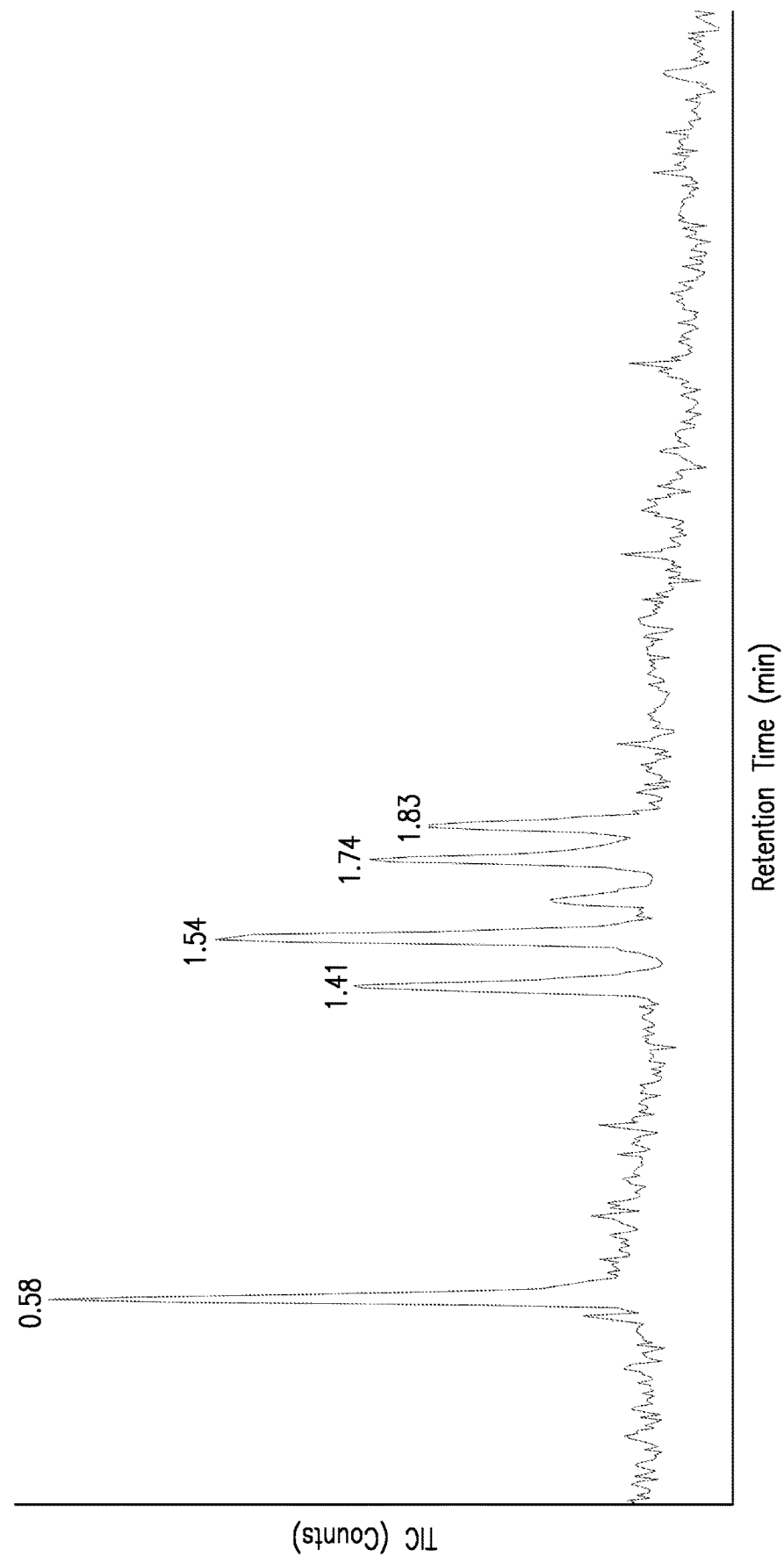
FIG. 10 is a spectrum derived from the assay described in Example 10.

FIG. 10 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.58 | 16232838 | 30.34 | 214 |
| 1.41 | 9956388 | 18.61 | 378 |
| 1.54 | 16126637 | 30.14 | 378 |
| 1.74 | 10037802 | 18.76 | 360 |
| 1.83 | 1153415 | 2.16 | 376 |

With approximately 50.90% with the mass 378/376.

Example 11: 1:5-80° C.

A. Ingredients
  164 mg thymoquinone
  43 mg harmaline
  2 mL EtOH
B. Reaction Conditions
  1. Combine thymoquinone, harmaline, and ethanol
  2. Mix until dissolved
  3. Put in −80° C. freezer overnight
  4. Remove from freezer and allow sample to return to room temperature
  5. Put in −40° C. freezer over the weekend
  6. Remove from freezer and allow sample to return to room temperature
  7. Add 5 µL of sample to 1 mL of EtOH, with mixing
  8. Add 10 µL of dilution to 0.75 mL LCMS grade water and 0.25 mL of LCMS grade acetonitrile

| LCMS column gradient: | | | |
|---|---|---|---|
| Solvent A | Water with 1% Formic Acid | | |
| Solvent B | Acetonitrile with 1% Formic Acid | | |
| Time (min) | Flow (mL/min) | % A | % B |
| 0 | 0.7 | 80 | 20 |
| 9 | 0.7 | 2 | 98 |
| 10 | 0.7 | 2 | 98 |
| 12 | 0.7 | 80 | 20 |

Figure 11:
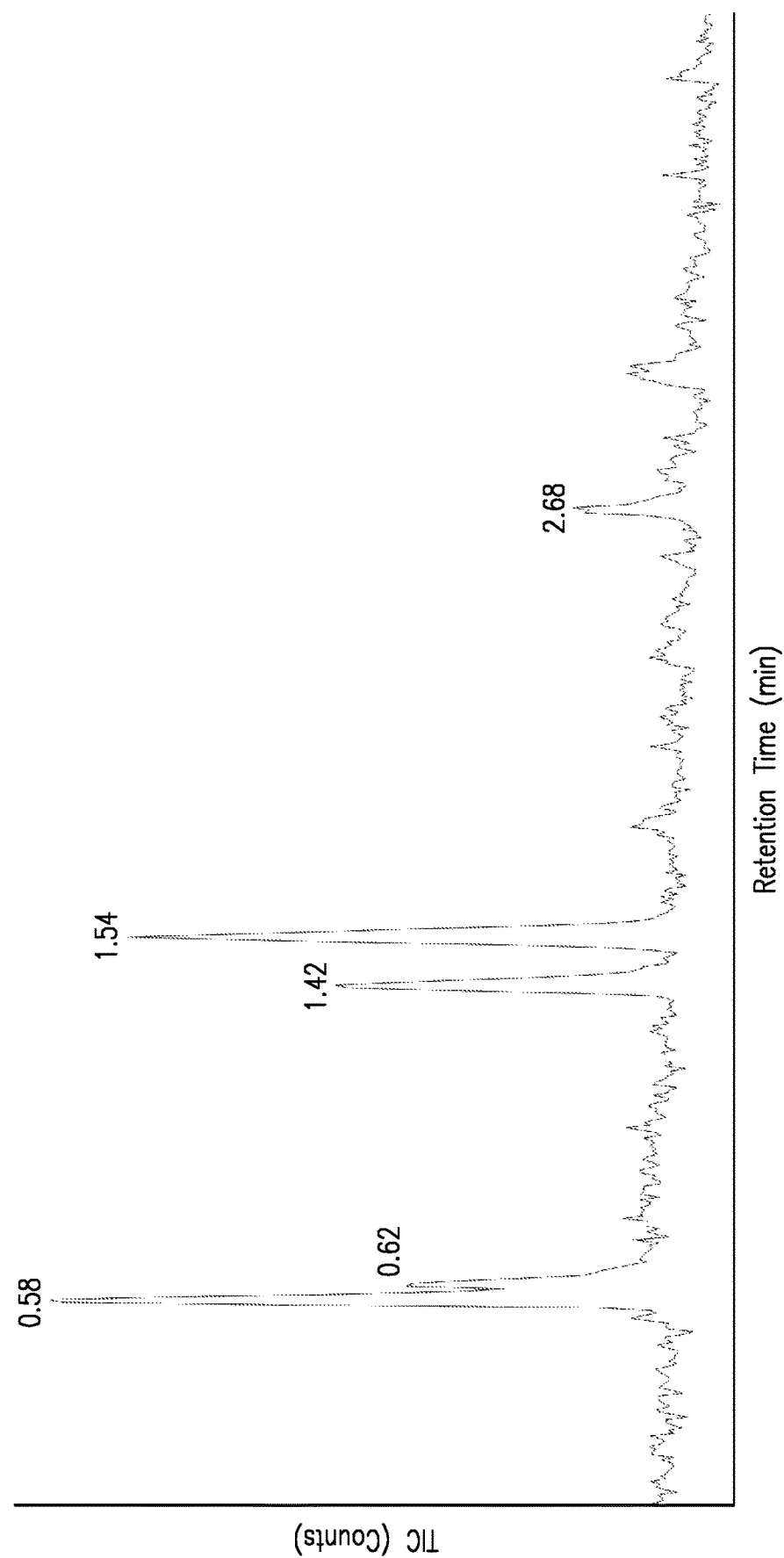
FIG. 11 is a spectrum derived from the assay described in Example 11.

FIG. 11 is the spectrum generated in this example. The following table lists the retention times, the areas under the important peaks, the % areas, and the mass of the corresponding reaction products.

| Retention Time (min) | Area | % Area | Mass |
|---|---|---|---|
| 0.58 | 23086000 | 29.61 | 214 |
| 0.62 | 9346882 | 11.99 | 212 |
| 1.42 | 15029988 | 19.28 | 378 |
| 1.54 | 25596606 | 32.83 | 378 |
| 2.68 | 4905235 | 6.29 | 524 |

With approximately 52.11% with the mass 378.

CONCLUSIONS

As is evident from the spectra and the area data from the tables of the examples, the low-temperature syntheses gave significantly higher quantities of the desirable end products having molecular weights of from about 360-380, and more particularly 360, 376, and 378. The initial peak in each case was residual harmaline (mass 214) and the products other than the desired products were very low in % Area and hence weight amounts. Thus, the low-temperature synthesis methods of the invention give much improved reaction product syntheses as compared with prior high-temperature methods.

We claim:

1. A method of preparing thymoquinone/harmaline reaction products comprising a thymoquinone moiety and a harmaline moiety, said method comprising the steps of mixing together thymoquinone and harmaline in a noninterfering solvent to yield a reaction mixture, and allowing said reaction mixture to stand a temperature of less than about 10° C. for a time period of from about 6 to 100 hours to yield said thymoquinone/harmaline reaction products.

2. The method of claim 1, said temperature being less than about 0° C.

3. The method of claim 2, said temperature being from about −10° C. to about −100° C.

4. The method of claim 1, including the step of reacting said thymoquinone and harmaline for a period of from about 4 hours-14 days.

5. The method of claim 4, said period being from about 6-100 hours.

6. The method of claim 1, including the step of carrying out said reaction so that the amount of reaction products having a molecular weight ranging from about 360-380 is greater than the amount of any other reaction product of different molecular weight.

7. The method of claim 6, at least about 35% by weight of said reaction products have molecular weights ranging from about 360-380.

8. The method of claim 1, including the step of carrying out said reaction so that the total amount of said reaction products having molecular weights of about 376 and about 378 is at least about 25% by weight of said reaction products.

9. The method of claim 8, including the step of carrying out said reaction so that the total amount of said reaction products having molecular weights of about 376 and about 378 is at least about 30% by weight of said reaction products.

10. The method of claim 1, said solvent selected from the group consisting of a C1-C4 alcohol, dimethyl sulfoxide, and mixtures thereof.

11. The method of claim 1, said reaction products including one or more of the following, or the solvates, esters, metal complexes, and salts thereof:

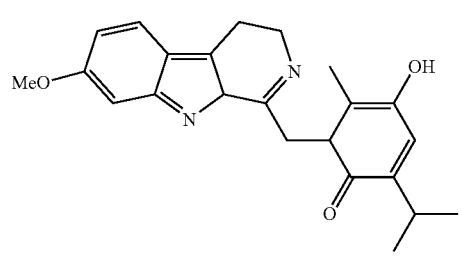

I

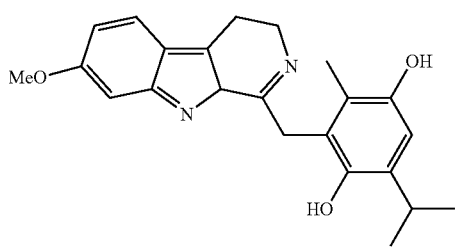

II

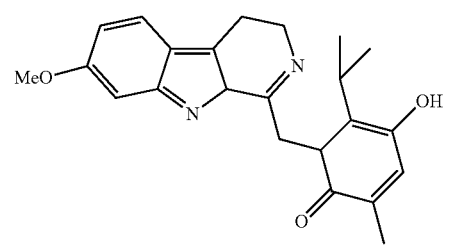

III

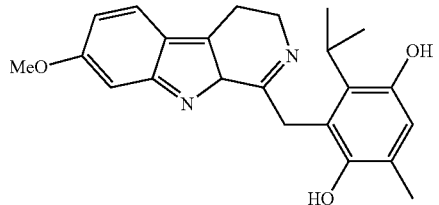

IV

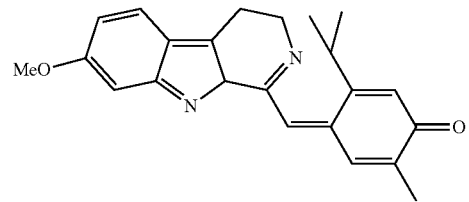

V

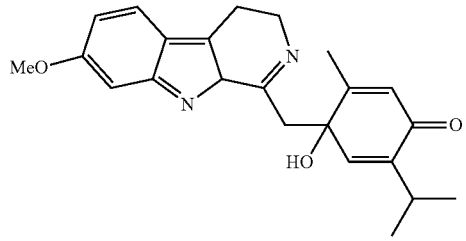

VI

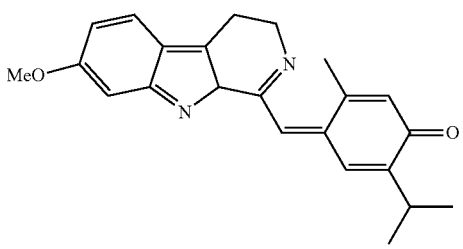

VII

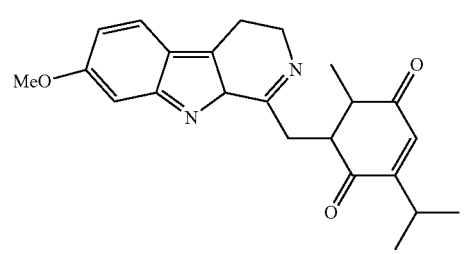

IA

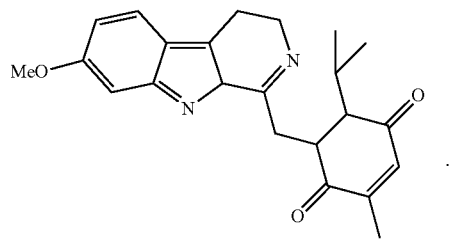

IIIA

* * * * *